United States Patent
Al-Ali et al.

(10) Patent No.: US 7,415,297 B2
(45) Date of Patent: Aug. 19, 2008

(54) PHYSIOLOGICAL PARAMETER SYSTEM

(75) Inventors: Ammar Al-Ali, Tustin, CA (US); John Graybeal, Grantville, PA (US); Massi E. Kiani, Laguna Niguel, CA (US); Michael Petterson, Dana Point, CA (US)

(73) Assignee: Masimo Corporation, Irvine, CA (US)

( * ) Notice: Subject to any disclaimer, the term of this patent is extended or adjusted under 35 U.S.C. 154(b) by 582 days.

(21) Appl. No.: 11/075,389

(22) Filed: Mar. 8, 2005

(65) Prior Publication Data

US 2005/0203352 A1   Sep. 15, 2005

Related U.S. Application Data

(60) Provisional application No. 60/551,165, filed on Mar. 8, 2004, provisional application No. 60/600,640, filed on Aug. 11, 2004.

(51) Int. Cl.
*A61B 5/1455* (2006.01)
(52) U.S. Cl. .................. 600/323; 340/511; 340/573.1
(58) Field of Classification Search ............ 600/300, 600/322, 323, 326; 340/511, 573.1
See application file for complete search history.

(56) References Cited

U.S. PATENT DOCUMENTS

| | | | |
|---|---|---|---|
| 4,453,218 A * | 6/1984 | Sperinde et al. ............ 600/331 |
| 4,960,128 A | 10/1990 | Gordon et al. | |
| 5,123,420 A * | 6/1992 | Paret ........................ 600/511 |
| 5,163,438 A | 11/1992 | Gordon et al. | |
| 5,337,744 A | 8/1994 | Branigan | |
| 5,431,170 A | 7/1995 | Mathews | |
| 5,452,717 A | 9/1995 | Branigan et al. | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,590,649 A | 1/1997 | Caro et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |

(Continued)

OTHER PUBLICATIONS

Bloom, Marc J., "Techniques to identify clinical contexts during automated data analysis", International Journal of Clinical Monitoring and Computing Netherlands, Feb. 1993, vol. 10, No. 1, pp. 17-22.

(Continued)

*Primary Examiner*—Eric F. Winakur
*Assistant Examiner*—Etsub D Berhanu
(74) *Attorney, Agent, or Firm*—Knobbe, Martens, Olson & Bear, LLP (57) ABSTRACT

A physiological parameter system has one or more parameter inputs responsive to one or more physiological sensors. The physiological parameter system may also have quality indicators relating to confidence in the parameter inputs. A processor is adapted to combine the parameter inputs, quality indicators and predetermined limits for the parameters inputs and quality indicators so as to generate alarm outputs or control outputs or both.

15 Claims, 8 Drawing Sheets

U.S. PATENT DOCUMENTS

| | | |
|---|---|---|
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,215,403 B1 * | 4/2001 | Chan et al. ............... 340/573.1 |
| 6,229,856 B1 | 5/2001 | Diab et al. |
| 6,236,872 B1 | 5/2001 | Diab et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,334,065 B1 | 12/2001 | Al-Ali et al. |
| 6,337,629 B1 | 1/2002 | Bader |
| 6,349,228 B1 | 2/2002 | Kiani et al. |
| 6,360,114 B1 | 3/2002 | Diab et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,449,501 B1 * | 9/2002 | Reuss ........................ 600/323 |
| 6,463,311 B1 | 10/2002 | Diab |
| 6,470,199 B1 | 10/2002 | Kopotic et al. |
| 6,501,975 B2 | 12/2002 | Diab et al. |
| 6,515,273 B2 | 2/2003 | Al-Ali |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,725,075 B2 | 4/2004 | Al-Ali |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 2002/0190863 A1 | 12/2002 | Lynn |
| 2004/0111014 A1 * | 6/2004 | Hickle ........................ 600/300 |

OTHER PUBLICATIONS

Horn, Werner, et al. "Effective Data Validation of High-Frequency Data: Time-Point-, Time-Interval-, And Trend-Based Methods", Computers in Biology and Medicine, Sep. 1997, vol. 27, No. 5, pp. 389-409.

* cited by examiner

PHYSIOLOGICAL PARAMETER SYSTEM

CROSS-REFERENCE TO RELATED APPLICATIONS

This application relates to and claims the benefit of prior U.S. Provisional Applications No. 60/551,165 titled Combined Physiological Parameter Monitor, filed Mar. 08, 2004 and No. 60/600,640 titled Physiological Parameter Controller, filed Aug. 11, 2004, both prior applications incorporated by reference herein.

BACKGROUND OF THE INVENTION

Pulse oximetry is a widely accepted noninvasive procedure for measuring the oxygen saturation level of arterial blood, an indicator of a person's oxygen supply. Early detection of a low blood oxygen level is critical in the medical field, for example in critical care and surgical applications, because an insufficient supply of oxygen can result in brain damage and death in a matter of minutes. A typical pulse oximetry system utilizes a sensor applied to a patient's finger. The sensor has an emitter configured with both red and infrared LEDs that project light through the finger to a detector so as to determine the ratio of oxygenated and deoxygenated hemoglobin light absorption. In particular, the detector generates first and second intensity signals responsive to the red and IR wavelengths emitted by the LEDs after absorption by constituents of pulsatile blood flowing within a fleshy medium, such as a finger tip. A pulse oximetry sensor is described in U.S. Pat. No. 6,088,607 titled Low Noise Optical Probe, which is assigned to Masimo Corporation, Irvine, Calif. and incorporated by reference herein.

Capnography comprises the continuous analysis and recording of carbon dioxide concentrations in the respiratory gases of patients. The device used to measure the $CO_2$ concentrations is referred to as a capnometer. $CO_2$ monitoring can be performed on both intubated and non-intubated patients. With non-intubated patients, a nasal cannula is used. Capnography helps to identify situations that can lead to hypoxia if uncorrected. Moreover, it also helps in the swift differential diagnosis of hypoxia before hypoxia can lead to irreversible brain damage. Pulse oximetry is a direct monitor of the oxygenation status of a patient. Capnography, on the other hand, is an indirect monitor that helps in the differential diagnosis of hypoxia so as to enable remedial measures to be taken expeditiously before hypoxia results in an irreversible brain damage.

SUMMARY OF THE INVENTION

Multiple physiological parameters, combined, provide a more powerful patient condition assessment tool than when any physiological parameter is used by itself. For example, a combination of parameters can provide greater confidence if an alarm condition is occurring. More importantly, such a combination can be used to give an early warning of a slowly deteriorating patient condition as compared to any single parameter threshold, which may not indicate such a condition for many minutes. Conditions such as hypovolemia, hypotension, and airway obstruction may develop slowly over time. A physiological parameter system that combines multiple parameters so as to provide an early warning could have a major effect on the morbidity and mortality outcome in such cases.

Further, a greater emphasis has been put on decreasing the pain level of patients on the ward. Accordingly, patients are often given an IV setup that enables the patient to increase the level of analgesia at will. In certain situations, however, the patient's input must be ignored so as to avoid over medication. Complications from over sedation may include hypotension, tachycardia, bradycardia, hypoventilation and apnea. A physiological parameter system that uses pulse oximetry monitoring of $SpO_2$ and pulse rate in conjunction with patient controlled analgesia (PCA) can aid in patient safety. Utilization of conventional pulse oximetry in conjunction with PCA, however, can result in the patient being erroneously denied pain medication. Conventional monitors are susceptible to patient motion, which is likely to increase with rising pain. Further, conventional monitors do not provide an indication of output reliability.

Advanced pulse oximetry is motion tolerant and also provides one or more indications of signal quality or data confidence. These indicators can be used as arbitrators in decision algorithms for adjusting the PCA administration and sedation monitoring. Further, advanced pulse oximetry can provide parameters in addition to oxygen saturation and pulse rate, such as perfusion index (PI). For example, hypotension can be assessed by changes in PI, which may be associated with changes in pulse rate. Motion tolerant pulse oximetry is described in U.S. Pat. No. 6,699,194 titled Signal Processing Apparatus and Method; signal quality and data confidence indicators are described in U.S. Pat. No. 6,684,090 titled Pulse Oximetry Data Confidence Indicator, both of which are assigned to Masimo Corporation, Irvine, Calif. and incorporated by reference herein.

One aspect of a physiological parameter system is a first parameter input responsive to a first physiological sensor and a second parameter input responsive to a second physiological sensor. A processor is adapted to combine the parameters and predetermined limits for the parameters so as to generate an alarm output.

Another aspect of a physiological parameter system is a parameter input responsive to a physiological sensor and a quality indicator input relating to confidence in the parameter input. A processor is adapted to combine the parameter input, the quality indicator input and predetermined limits for the parameter input and the quality indicator input so as to generate a control output.

A physiological parameter method comprises the steps of inputting a parameter responsive to a physiological sensor and inputting a quality indicator related to data confidence for the parameter. A control signal is output from the combination of the parameter and the quality indicator. The control signal is adapted to affect the operation of a medical-related device.

DETAILED DESCRIPTION OF THE PREFERRED EMBODIMENTS

Figure 1:
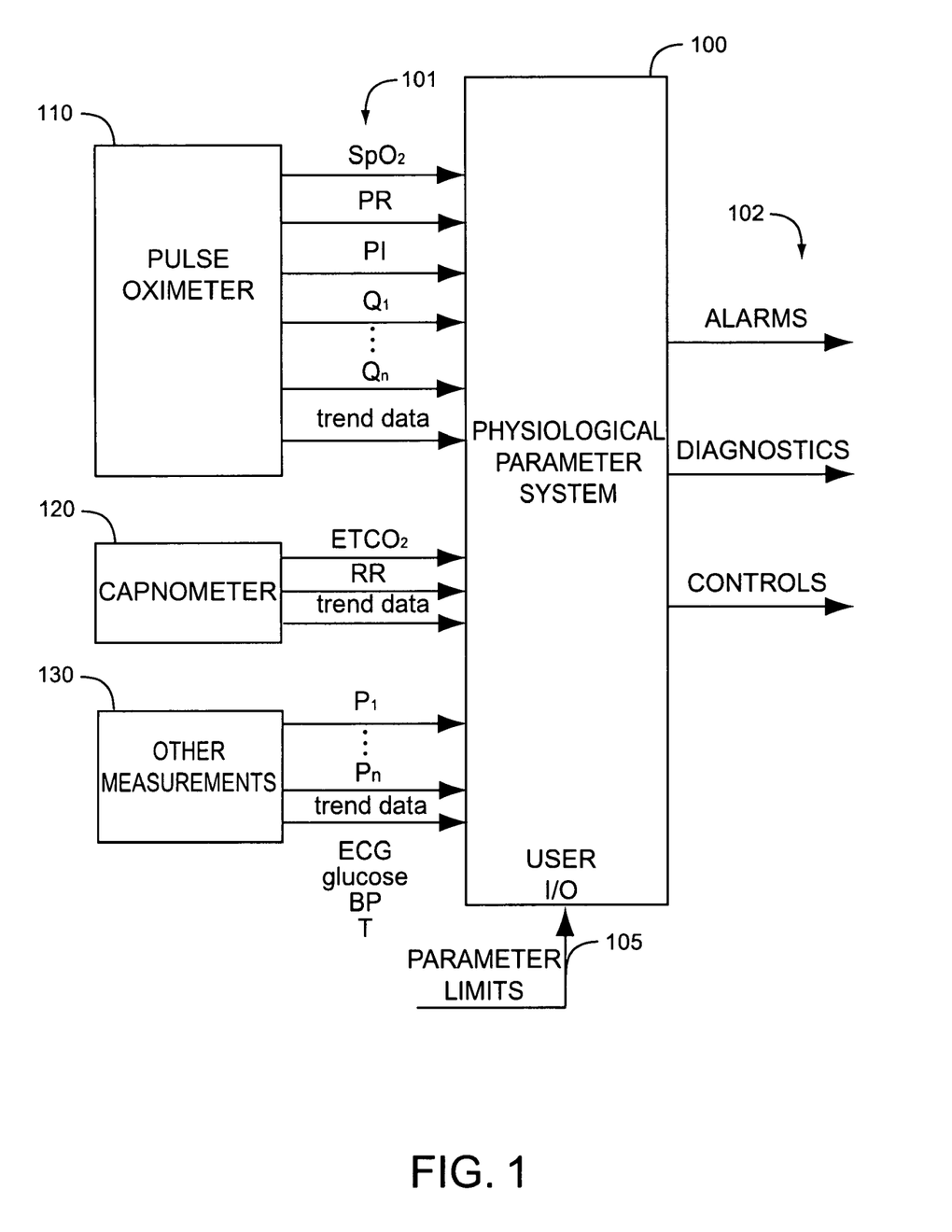
FIG. 1 is a general block diagram of a physiological parameter system having alarm, diagnostic and control outputs.

FIG. 1 illustrates a physiological parameter system 100, which may comprise an expert system, a neural-network or a logic circuit, for example; The physiological parameter system 100 has as inputs 101 one or more parameters from one or more physiological measurement devices, such as a pulse oximeter 110 and/or a capnometer 120. Pulse oximeter parameters may include oxygen saturation ($SpO_2$), perfusion index (PI), pulse rate (PR), various signal quality and/or data confidence indicators (Qn) and trend data, to name a few. Capnography parameter inputs may include, for example, an exhaled carbon dioxide waveform, end tidal carbon dioxide ($ETCO_2$) and respiration rate (RR). Signal quality and data confidence indicators are described in U.S. Pat. No. 6,684,090 cited above. The physiological parameter system 100 may also have parameter limits 105, which may be user inputs, default conditions or otherwise predetermined thresholds within the system 100.

The inputs 101 are processed in combination to generate one or more outputs 102 comprising alarms, diagnostics and controls. Alarms may be used to alert medical personnel to a deteriorating condition in a patient under their care. Diagnostics may be used to assist medical personnel in determining a patient condition. Controls may be used to affect the operation of a medical-related device. Other measurement parameters 130 that can be input to the monitor may include or relate to one or more of ECG, blood glucose, blood pressure (BP), temperature (T), HbCO and MetHb, to name a few.

Figure 2:
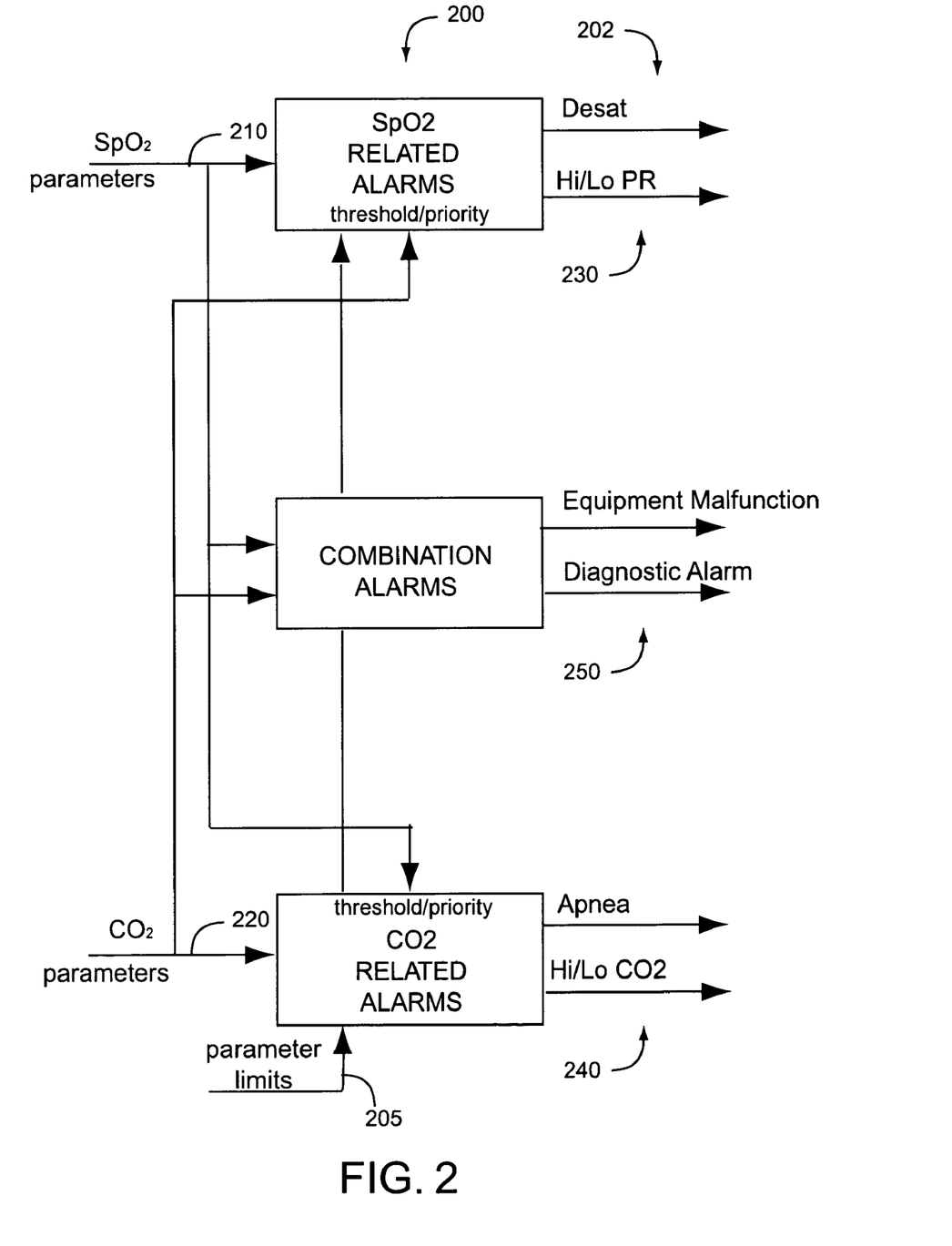
FIG. 2 is a block diagram of a physiological parameter system combining pulse oximetry and capnography and providing alarm outputs.

FIG. 2 illustrates one embodiment of a physiological parameter system 200 combining pulse oximetry parameter inputs 210 and capnography parameter inputs 220 so as to generate alarm outputs 202. Parameter limits 205 may be user inputs, default conditions or otherwise predetermined alarm thresholds for these parameters 210, 220. The alarms 202 are grouped as pulse oximetry related 230, capnography related 240 and a combination 250. For example, a pulse oximetry alarm 230 may be related to percent oxygen saturation and trigger when oxygen saturation falls below a predetermined percentage limit. A capnography alarm 240 may be related to $ETCO_2$ and trigger when $ETCO_2$ falls below or rises above a predetermined mm Hg pressure limit. A combination alarm 250 may indicate a particular medical condition related to both pulse oximetry and capnography or may indicate a malfunction in either instrument.

Figure 3:
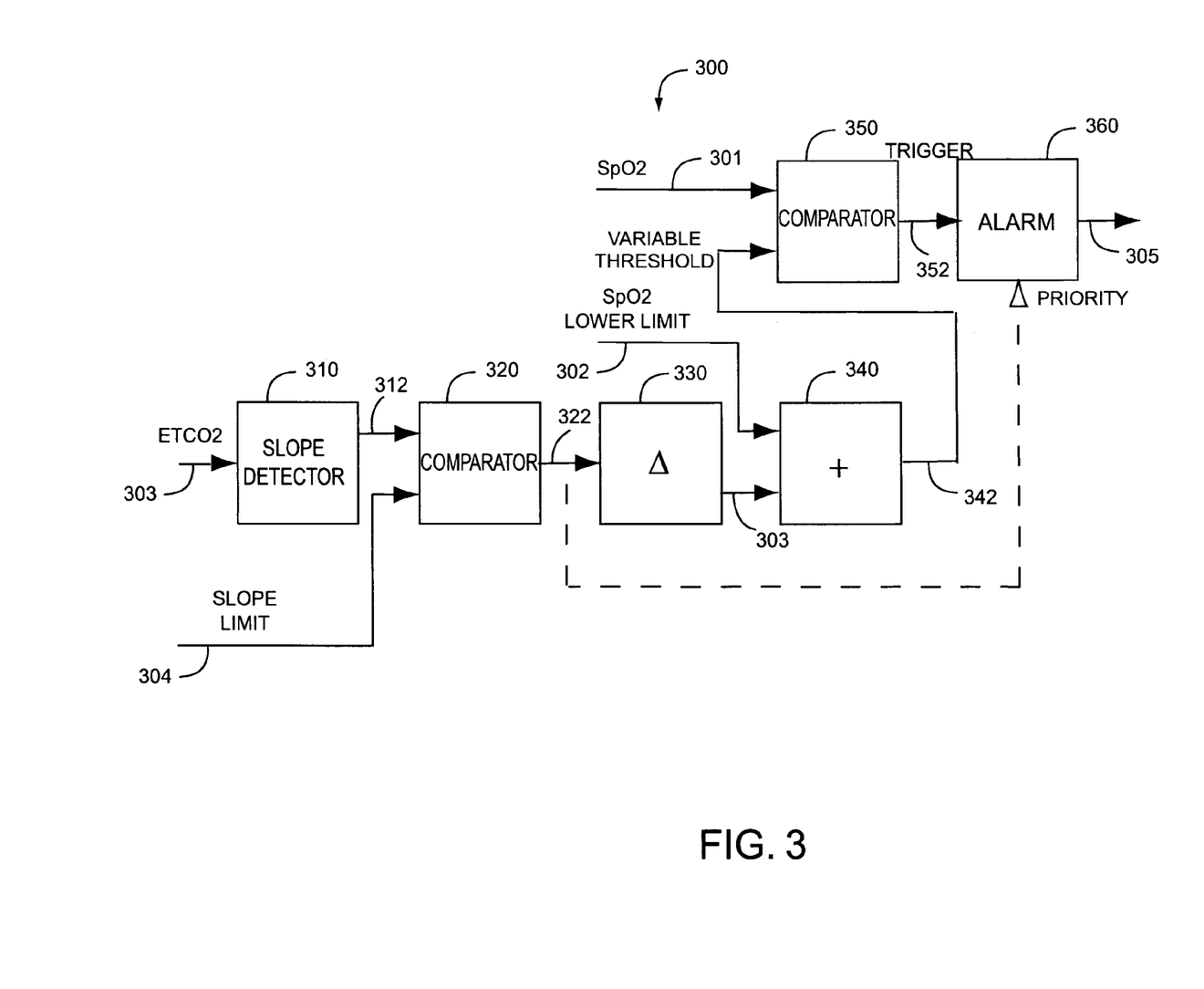
FIG. 3 is a block diagram of a saturation limit alarm enhanced by $ETCO_2$ measurements.

FIG. 3 illustrates a $SpO_2$ alarm embodiment 300 that is responsive to $ETCO_2$. In particular, a $SpO_2$ alarm 305 may be triggered sooner and may indicate a high priority if $ETCO_2$ 303 is falling. That is, if $ETCO_2$ 303 is trending down above a certain rate, the $SpO_2$ alarm 305 is triggered at a higher percentage oxygen saturation threshold and alerts a caregiver to the possibility of a serious condition, e.g. a pulmonary embolism.

As shown in FIG. 3, a slope detector 310 determines the slope 312 of the $ETCO_2$ input 303. A slope comparator 320 compares this slope 312 to a predetermined slope limit 304. If the downward trend of $ETCO_2$ 303 is great enough, a delta value 303 is added 340 to the $SpO_2$ lower limit 302 to generate a variable threshold 342. A threshold comparator 350 compares this variable threshold 342 to the $SpO_2$ input 301 to generate a trigger 352 for the $SpO_2$ alarm 305. The alarm volume, modulation or tone may be altered to indicate priority, based upon the slope comparator output 322.

Figure 4:
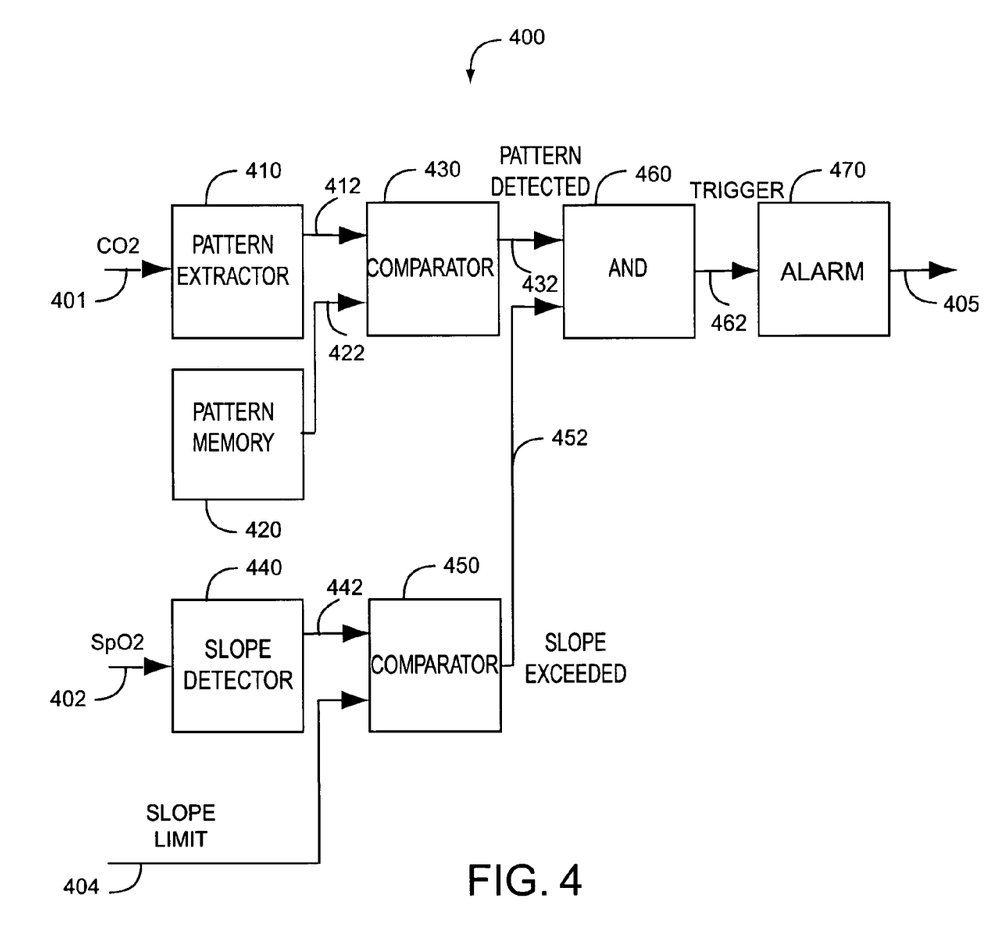
FIG. 4 is a block diagram of a $CO_2$ waveform alarm enhanced by $SPO_2$ measurements.

FIG. 4 illustrates a $CO_2$ alarm embodiment 400 that is responsive to $SpO_2$. In particular, morphology of the input $CO_2$ waveform 401 is utilized to trigger an alarm 405, and that alarm is also responsive to a falling $SpO_2$ 402. That is, if a pattern in the expired $CO_2$ waveform is detected and $SpO_2$ is trending down above a certain rate, then an alarm is triggered. For example, an increasing slope of the $CO_2$ plateau in combination with a downward trend of $SpO_2$ may trigger an alarm and alert a caregiver to the possibility of an airway obstruction.

As shown in FIG. 4, a pattern extractor 410 identifies salient features in the $CO_2$ waveform and generates a corresponding feature output 412. A pattern memory 420 stores one or more sets of predetermined waveform features to detect in the $CO_2$ input 401. The pattern memory 420 is accessed to provide a feature template 422. A feature comparator 430 compares the feature output 412 with the feature template 422 and generates a match output 432 indicating that a specific shape or pattern has been detected in the $CO_2$ waveform 401. In addition, a slope detector 440 determines the slope 442 of the $SpO_2$ input 402. A slope comparator 450 compares this slope 442 to a predetermined slope limit 404. If the downward trend of $SpO_2$ 402 is great enough, a slope exceeded output 452 is generated. If both the match output 432 and the slope exceeded output 452 are each asserted or "true," then a logical AND 460 generates a trigger output 462 to the alarm 470, which generates an alarm output 405.

Figure 5:
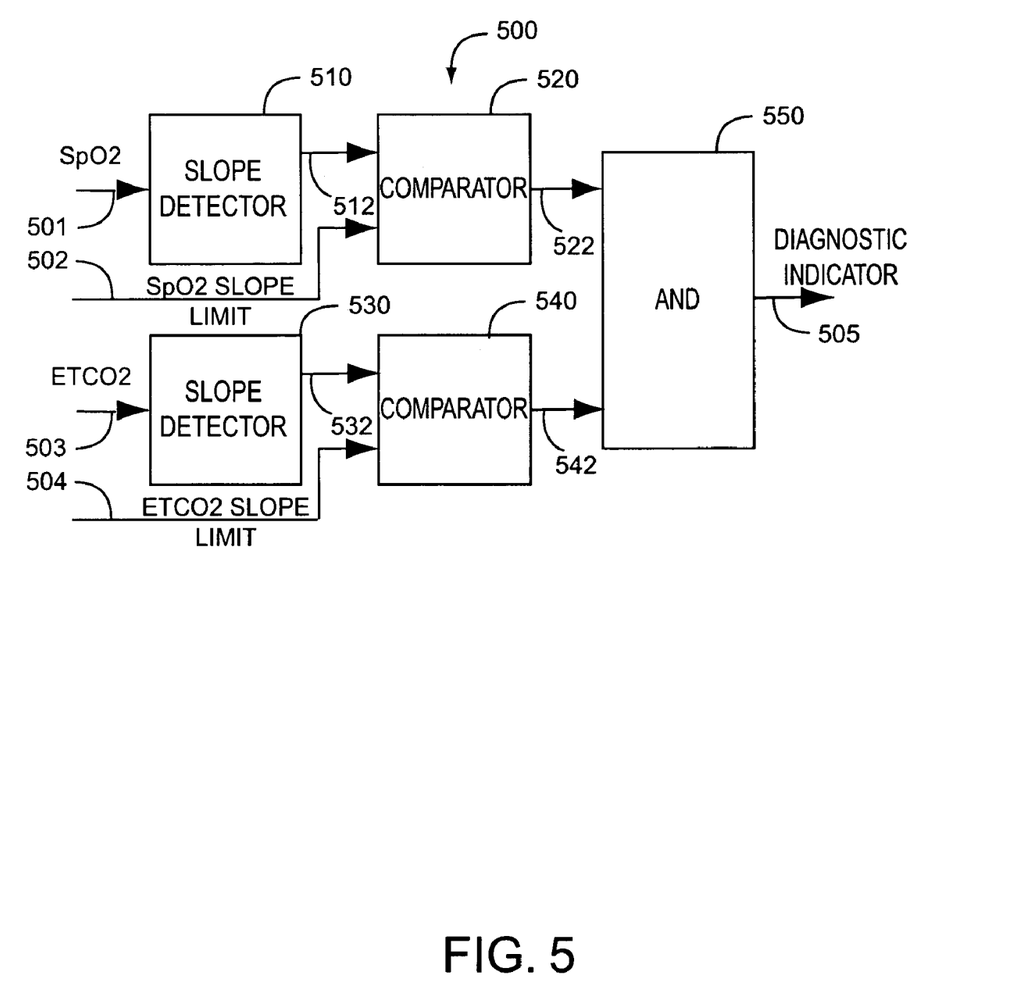
FIG. 5 is a block diagram of a physiological parameter system combining pulse oximetry and capnography and providing a diagnostic output.

FIG. 5 illustrates a combination embodiment 500 having a diagnostic output 505 responsive to both $SpO_2$ 501 and $ETCO_2$ 503 inputs. A $SpO_2$ slope detector 510 determines the slope 512 of the $SpO_2$ input 501 and can be made responsive to a negative slope, a positive slope or a slope absolute value. A first comparator 520 compares this slope 512 to a predetermined $SpO_2$ slope limit 502. If the trend of $SpO_2$ 501 is great enough, a $SPO_2$ slope exceeded output 522 is asserted. Likewise, an $ETCO_2$ slope detector 530 determines the slope 532 of the $ETCO_2$ input 503. A second comparator 540 compares this slope 532 to a predetermined $ETCO_2$ slope limit 504. If the downward trend of $ETCO_2$ 501 is great enough, an $ETCO_2$ slope exceeded output 542 is asserted. If both slope exceeded outputs 522, 542 are asserted or "true," a diagnostic output 505 is asserted.

In one embodiment, the slope detectors 510, 530 are responsive to a negative trend in the $SpO_2$ 501 and $ETCO_2$ 503 inputs, respectively. Accordingly, the diagnostic output 505 indicates a potential embolism or cardiac arrest. In another embodiment, the $SpO_2$ slope detector 510 is responsive to negative trends in the $SpO_2$ 501 input, and the $ETCO_2$ slope detector 530 is responsive to a positive trend in the $ETCO_2$ 503 input. Accordingly, the diagnostic output 505 indicates a potential airway obstruction. The diagnostic output 505 can trigger an alarm, initiate a display, or signal a nursing station, to name a few.

Figure 6A:
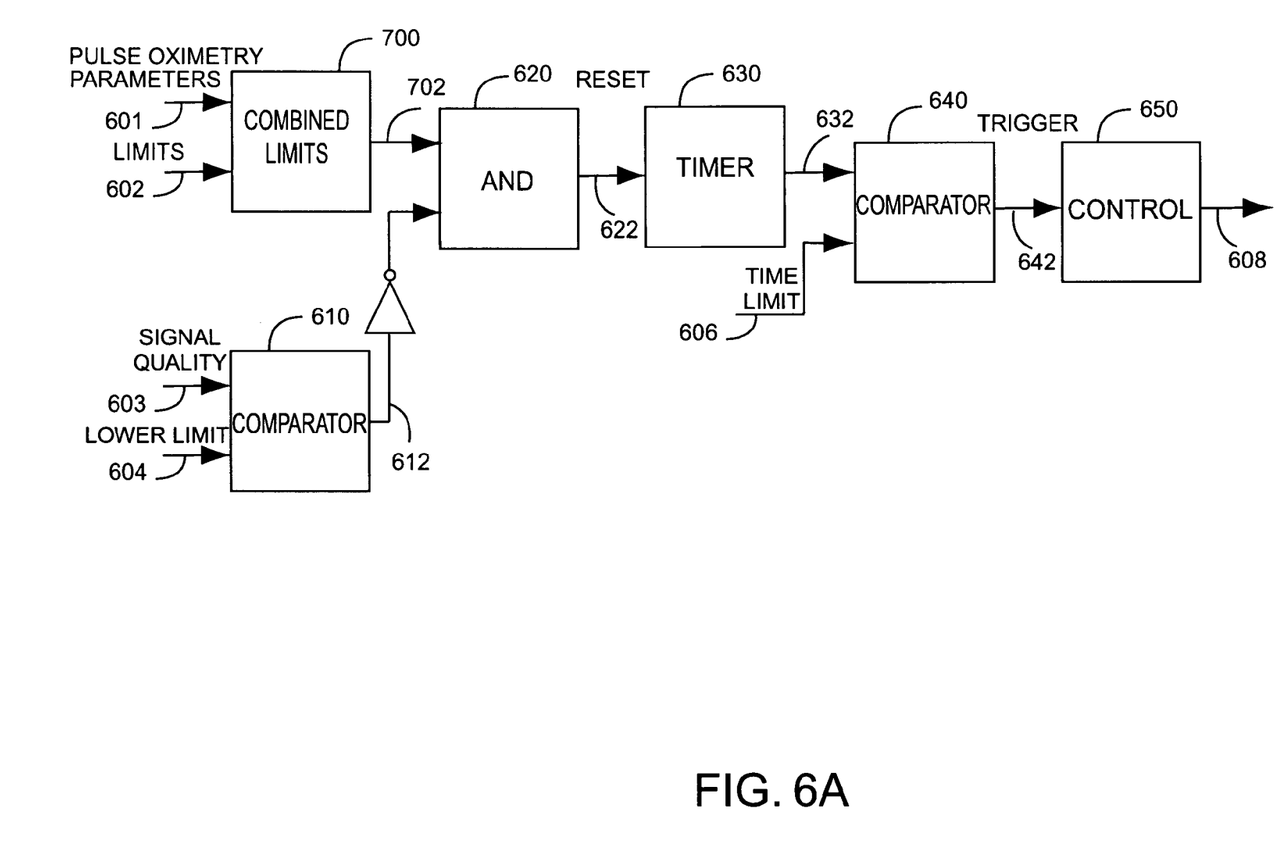
FIGS. 6-7 are block diagrams of a physiological parameter system utilizing pulse oximetry to control patient controlled analgesia (PCA).
Figure 6B:
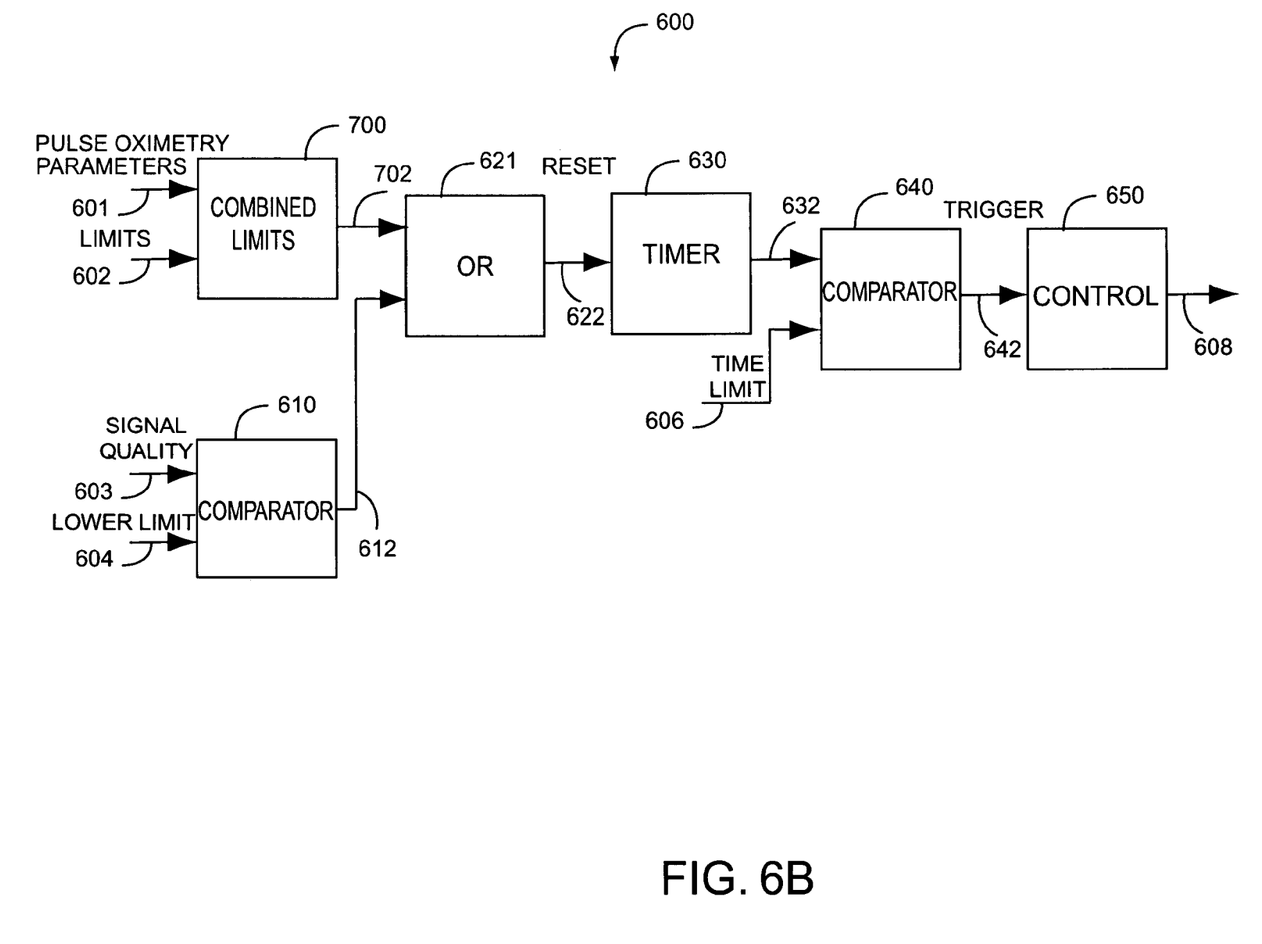

FIGS. 6A-B illustrate a physiological parameter system 600 utilizing pulse oximetry to control patient controlled analgesia (PCA). In particular embodiments, a control output 608 is responsive to pulse oximetry parameters 601 only if signal quality 603 is above a predetermined threshold 604. In FIG. 6A, the control output 608 can be used to lock-out patient controlled analgesia (PCA) if pulse oximetry parameter limits have been exceeded. If signal quality is so low that those parameters are unreliable, however, PCA is advantageously allowed. That is, the pulse oximeter parameters are not allowed to lock-out PCA if those parameters are unreliable. By contrast, in FIG. 6B, the control output 608 can be used to advantageously lock-out or disable patient controlled analgesia (PCA) if pulse oximetry parameter limits have been exceeded or if signal quality is so low that those parameters are unreliable.

As shown in FIG. 6A, pulse oximetry parameters 601 and corresponding limits 602 for those parameters are one set of inputs and a signal quality measure 603 and a corresponding lower limit 604 for signal quality are another set of inputs. The parameters 601 and corresponding limits 602 generate a combined output 702 that is asserted if any of the pulse oximetry parameter limits are exceeded. A comparator 610 compares the signal quality 603 input with a lower limit 604 generating a quality output 612 that is asserted if the signal quality 603 drops below that limit 604. An AND logic 620 generates a reset 622 if the combined output 702 is asserted and the quality output 612 is not asserted. The reset 622 resets the timer 630 to zero. A comparator 640 compares the timer output 632 to a predetermined time limit 606 and generates a trigger 642 if the time limit is exceeded. The trigger 642 causes the control 650 to generate the control output 608, enabling a patient controlled analgesia (PCA), for example. In this manner, the PCA is enabled if all monitored parameters are within set limits and signal quality is above its lower limit for a predetermined period of time.

As shown in FIG. 6B, the combined output 702, quality output 612, reset 622, timer 630, comparator 640 and control 650 are generated as described with respect to FIG. 6A, above. An OR logic 621 generates a reset 622 if either the combined output 702 or the quality output 612 is asserted. In this manner, the PCA is disabled for a predetermined period of time if any of the monitored parameters are outside of set limits or the signal quality is below its lower limit.

Figure 7:
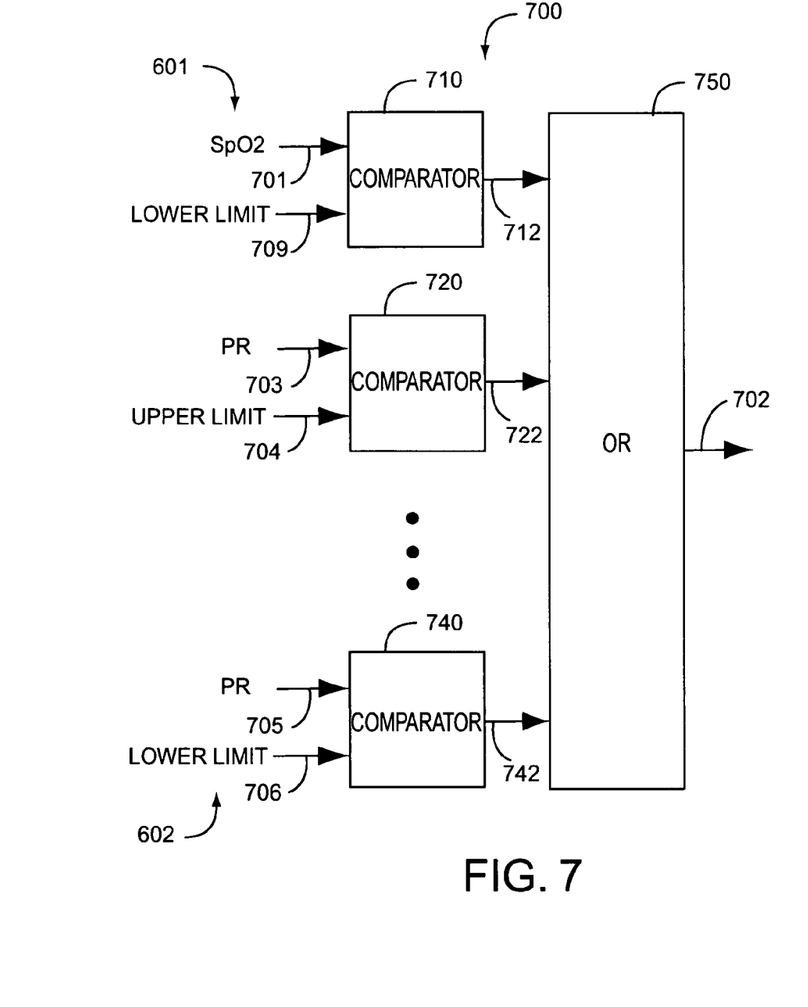

FIG. 7 illustrates combined limits 700 having $SpO_2$ parameters 601 and corresponding thresholds 602 as inputs and providing a combination output 702. In particular, if any parameter 601 exceeds its corresponding limit 602, the output of the corresponding comparator 710, 720, 740 is asserted. An OR logic 750 is responsive to any asserted output 712, 722, 742 to asserted the combined output 702. For example, the combined output 702 may be asserted if $SpO_2$ 701 falls below a lower limit 709, pulse rate (PR) 703 rises above an upper limit 704 or PR 703 falls below a lower limit 706.

A physiological parameter system has been disclosed in detail in connection with various embodiments. These embodiments are disclosed by way of examples only and are not to limit the scope of the claims that follow. One of ordinary skill in the art will appreciate many variations and modifications. For example, the control output 608 (FIGS. 6B) can be used to control (titrate) delivered, inspired oxygen levels to patients based upon pulse oximetry parameters, unless signal quality is so low that those parameters are unreliable. One of ordinary skill in the art will also recognize that the control output 608 (FIGS. 6B) can be used to control patient delivery of any of various pharmacological agents and/or medical gases.

What is claimed is:

1. A physiological parameter system comprising:
a first parameter input responsive to a first physiological sensor;
a second parameter input responsive to a second physiological sensor;
a plurality of predetermined limits for said parameters;
a processor adapted to combine said parameters and said limits so as to generate an alarm output;
a variable threshold responsive to said second parameter, said alarm output responsive to said first parameter and said variable threshold; and
a predetermined limit related to said second parameter, wherein said alarm output is triggered below said variable threshold, and
wherein said variable threshold is raised in response to said second parameter and said predetermined limit.

2. The physiological parameter system according to claim 1 wherein:
said first parameter is $SpO_2$,
said second parameter is $ETCO_2$, and
said variable threshold is a lower limit for $SpO_2$ that is raised in response to a downward trend in $ETCO_2$ at a rate greater than said predetermined limit.

3. A physiological parameter system comprising:
a first parameter input responsive to a first physiological sensor;
a second parameter input responsive to a second physiological sensor;
a plurality of predetermined limits for said parameters; and
a processor adapted to combine said parameters and said limits so as to generate an alarm output;
a pattern detector having a detection output responsive to said first parameter,
said alarm output responsive to said detection output;
a slope detector output responsive to said second parameter; and
a predetermined slope limit responsive to said slope detector output,
wherein said alarm output is triggered only if said slope detector output exceeds said slope limit.

4. The physiological parameter system according to claim 3 wherein:
said first parameter is $ETCO_2$,
said second parameter is $SpO_2$, and
said alarm output is responsive to $ETCO_2$ morphology only when there is a sufficient downward trend in $SpO_2$.

5. A physiological parameter system comprising:
a parameter input responsive to a physiological sensor;
a quality indicator in input relating to confidence in said parameter input;
a plurality of predetermined limits for said parameter input and said quality indicator input; and
a processor adapted to combine said inputs and said limits so as to generate a control output, wherein said control output disables patient controlled analgesia when confidence in said parameter input is low.

6. The physiological parameter system according to claim 5 wherein said control output prevents said parameter input from disabling patient controlled analgesia when said quality indicator indicates confidence is low.

7. A physiological parameter method comprising the steps of:
inputting a parameter responsive to a physiological sensor;
inputting a quality indicator related to data confidence for said parameter;
outputting a control signal from the combination of said parameter and said quality indicator,
wherein said control signal is adapted to affect the operation of a medical-related device, wherein said parameter and said quality indicator are derived from a pulse oximetry sensor, and wherein said outputting step comprises configuring said control signal to conditionally disable said medical-related device, and
regulating said control signal in response to said quality indicator.

8. The physiological parameter method according to claim 7 wherein said regulating substep comprises the substep of disabling a shut-off signal when confidence in said parameter is low.

9. The physiological parameter method according to claim 8 wherein said regulating substep comprises the substep of enabling a shut-off signal when confidence in said parameter is high.

10. An override of a patient selection input to a patient controlled medical device, the override comprising:
   a first input configured to receive a parameter signal indicative of a physiological parameter of a patient being monitored;
   a second input configured to receive a confidence signal indicative of a confidence that the parameter signal actually indicates the physiological parameter;
   an output configured to transmit an output signal formatted to prevent a patient selection in a patient controlled medical device; and
   a processor in communication with said first and second input and said output and configured to process said parameter signal and said confidence signal to output said output signal.

11. The override of claim 10, wherein said patient controlled medical device comprises a patient controlled analgesia device.

12. The override of claim 10, wherein the parameter signal is indicative of a blood oxygen saturation of said patient.

13. An override of a patient selection input to a patient controlled medical device, the override comprising:
   a first input configured to receive a first parameter signal indicative of a first physiological parameter of a patient being monitored;
   a second input configured to receive a second parameter signal indicative of a second physiological parameter of said patient, said first and second parameters being different from one another;
   an output configured to transmit an output signal formatted to prevent a patient selection in a patient controlled medical device; and
   a processor in communication with said first and second input and said output and configured to process said first and second parameter signals, and based at least upon predetermined limit values for said first and second parameter signals, to output said output signal, wherein at least some of said predetermined limit values comprise variable limits dependent upon at least one of said first and second parameters.

14. The override of claim 13, wherein said first parameter signal is indicative of $SpO_2$, said second parameter signal is indicative of $ETCO_2$.

15. The override of claim 14, wherein said variable limits comprise a higher percent $SpO_2$ limit when $ETCO_2$ is trending downward at a rate greater than a predetermined limit.

* * * * *

UNITED STATES PATENT AND TRADEMARK OFFICE
CERTIFICATE OF CORRECTION

PATENT NO. : 7,415,297 B2
APPLICATION NO. : 11/075389
DATED : August 19, 2008
INVENTOR(S) : Ammar Al-Ai et al.

It is certified that error appears in the above-identified patent and that said Letters Patent is hereby corrected as shown below:

At column 3, line 6, delete "example," and insert -- example. --, therefor.

At column 4, line 33, delete "SPO$_2$" and insert -- SpO$_2$ --, therefor.

At column 6, line 36, in Claim 5, after "indicator" delete "in".

Signed and Sealed this

Fourteenth Day of April, 2009

JOHN DOLL
*Acting Director of the United States Patent and Trademark Office*